United States Patent [19]

Robinson et al.

[11] 4,240,409
[45] Dec. 23, 1980

[54] APPARATUS FOR ASSISTING CIRCULATION OF BLOOD

[75] Inventors: William J. Robinson, Wellesley; Victor L. Poirier, Chelmsford; Benedict D. T. Daly, Wellesley, all of Mass.

[73] Assignee: Thermo Electron Corporation, Waltham, Mass.

[21] Appl. No.: 13,636

[22] Filed: Feb. 21, 1979

[51] Int. Cl.³ .............................................. A61B 19/00
[52] U.S. Cl. ............................. 128/1 D; 128/DIG. 3; 417/384; 3/1.7
[58] Field of Search ................ 128/1 D, 273, DIG. 3; 3/117; 417/383, 384, 386, 388, 394

[56] References Cited

U.S. PATENT DOCUMENTS

| 3,410,263 | 11/1968 | McGinnis | 128/1 D |
| 3,630,644 | 12/1971 | Bellhouse | 417/388 |
| 3,822,968 | 7/1974 | Makarov et al. | 417/394 |
| 3,883,272 | 5/1975 | Puckett | 417/383 |
| 4,023,468 | 5/1977 | Poirier | 92/13.2 |
| 4,034,742 | 7/1977 | Thoma | 128/1 D |
| 4,047,849 | 9/1977 | Clay | 417/388 |
| 4,086,665 | 5/1978 | Poirier | 3/1.4 |
| 4,104,005 | 8/1978 | Poirier | 417/394 |
| 4,131,604 | 12/1978 | Szycher | 128/1 D |

OTHER PUBLICATIONS

"Assisted Circulation I. The Arterial Counterpulsator", Clauss et al., J. Thoracic and Cardiovas. Surg., vol. 41, No. 4, 4/61, pp. 447-458.
"The Windkesselventricle with Guiding Balloon as a New Approach for Assisted Circulation", Unger et al., Medical Instrumention, vol. 10, No. 5, 1976, pp. 256-259.

Primary Examiner—Robert W. Michell
Assistant Examiner—J. L. Kruter
Attorney, Agent, or Firm—Herbert E. Messenger; James L. Neal

[57] ABSTRACT

Apparatus is disclosed for mechanically assisting circulation of blood in a patient for periods of up to a week or two until the patient's heart strengthens sufficiently to take over the full workload. The circulatory assist device includes a valveless pump with a flexible bladder, a pneumatic driver for applying pressure pulses to the bladder, and a single flexible conduit for conveying blood between the patient and the pump. In use the pump and driver are mounted external to the patient's body and the flexible conduit is connected to the pump and in end-to-side relationship with a major blood vessel on that side of the heart, either right or left, which is in need of support. The circulatory assist device is operable either synchronously with the patient's heartbeat wherein the pump bladder fills as the heart ejects, then ejects in response to a pressure pulse from the driver while the heart is at rest, or asynchronously at a fixed rate if an irregular heartbeat of the patient precludes synchronous operation. The device, which can support up to about half of the workload of the heart, is easy to implant and remove and may be used to assist blood circulation in children as well as adults.

6 Claims, 3 Drawing Figures

APPARATUS FOR ASSISTING CIRCULATION OF BLOOD

BACKGROUND OF THE INVENTION

This invention relates to apparatus for assisting circulation of blood and more particularly to a device for providing circulatory assistance to patients in ventricular failure whose hearts cannot maintain a blood circulation adequate to sustain life or to patients with acute coronary occlusion to reduce workload of the heart and limit the damage while collateral circulation develops.

The need for devices to provide mechanical assistance for failing blood circulatory systems has been recognized for several years and a number of blood pumps have been developed and tested. One clinically accepted method of assistance is use of an intraaortic balloon pump, an inflatable balloon attached to the end of a catheter and positioned in the thoracic aorta of a patient. The balloon pump is operated in a counterpulsation mode wherein the balloon is inflated with a gas immediately following left ventricular ejection and deflated just prior to the next ventricular ejection, thus imparting a pumping force to the blood and reducing the load on the left ventricle. Balloon pumps, though helpful, are limited to support of the left ventricle only, typically operate only synchronously with the heartbeat of the patient, and can provide support for only a small fraction of the total workload of the left ventricle. Other drawbacks of these devices include possible blockage of arterial branches to major organs during inflation or removal/insertion of the balloon, particularly with children, and the creation of emboli during their insertion or use by fragmenting plaque in the blood vessels.

Another assist device which has been tested clinically is a left ventricular assist device (LVAD) which includes an implantable pump which may be connected between the left ventricle and aorta of a person such as a patient in acute left ventricular failure following open-heart surgery. This pump, which is similar to that described in U.S. Pat. No. 4,104,005 issued in the name of V. L. Poirier, has a flexible bladder which fills from the left ventricle through an inlet valve. Pneumatic pulses, either synchronous with the heartbeat or asynchronous at a fixed rate, apply pressure to collapse the bladder and eject blood through an outlet valve into the aorta. The LVAD, like the balloon pump, is designed to assist the left ventricle only but in contrast thereto may assume total workload of the left ventricle. However, because of the size of the LVAD pump and a requirement that it be implanted, use of the LVAD is restricted to adults. Also the LVAD pump is considerably more invasive than the balloon pump and usually requires a second rather extensive surgical procedure for removal at the end of its period of use of from about one day to two weeks.

A third apparatus for mechanically assisting circulation of blood is shown in U.S. Pat. No. 4,034,742 issued to H. Thoma. The apparatus described in this patent comprises an implantable pumping chamber connectable to the aorta by a conduit through which blood flows to and from the aorta, and an inflatable balloon which is positioned in the aorta downstream of the conduit connection point. In operation, the balloon is inflated during ejection of blood by the left ventricle (systole), blocking the aorta, and blood is sucked into the pumping chamber. This is followed by deflation of the balloon and application of a pneumatic pulse to the pumping chamber during the period of rest of the heart (diastole), which forces blood through the aorta and cardiovascular system of the patient. This apparatus operates in synchronism with the heartbeat and, like the above-described devices, is usable only with the left ventricle and is ill-suited for use with children. Possible imposition of back pressure on the heart by the balloon during filling of the pumping chamber is a further drawback of this apparatus.

Accordingly, it is an object of this invention to provide improved apparatus for assisting circulation of blood in a patient.

It is also an object of the invention to provide a ventricular assist device suitable for supporting the right or left side of the heart.

A further object of the invention is to provide apparatus for assisting circulation of blood which is suited for use with children as well as adults.

Another object of the invention is to provide apparatus for assisting circulation of blood which is simple to implant and remove and which does not impede normal blood flow within blood vessels of a patient.

It is an additional object of the invention to provide apparatus which in addition to fulfilling the above objectives, is operable synchronously or asynchronously with the heartbeat.

SUMMARY OF THE INVENTION

Apparatus is provided for assisting circulation of the blood of a patient whose heart is temporarily unable to maintain adequate circulation or avoid further damage without support. The circulatory assist device includes a non-implantable valveless blood pump for admitting and ejecting blood through one end of the pump, a pneumatic driver for delivering pressure pulses to compress and release a flexible bladder within the pump, and a flexible conduit for carrying blood between the interior of the bladder and a major blood vessel of the patient. One end of the flexible conduit is connected to the pump and, during use, the other end is attached to the side of a selected major blood vessel on the right or left side of the heart. The end-to-side attachment of the conduit to the blood vessel may be accomplished by a simple implantation procedure and results in an attachment which does not impede normal blood flow within the selected vessel. The circulatory assist device is operable in synchronism with the patient's hearbeat wherein the bladder of the pump fills as the heart ejects, then empties to provide additional force to circulate blood and relieve a significant portion of the workload of the heart. It may also operate asynchronously at a fixed rate if an irregular heartbeat precludes synchronous operation. To limit the maximum movement of the bladder walls during operation, the assist device also preferably includes a pulse limiter between the pneumatic driver and the pump.

DETAILED DESCRIPTION OF THE INVENTION

Figure 1:
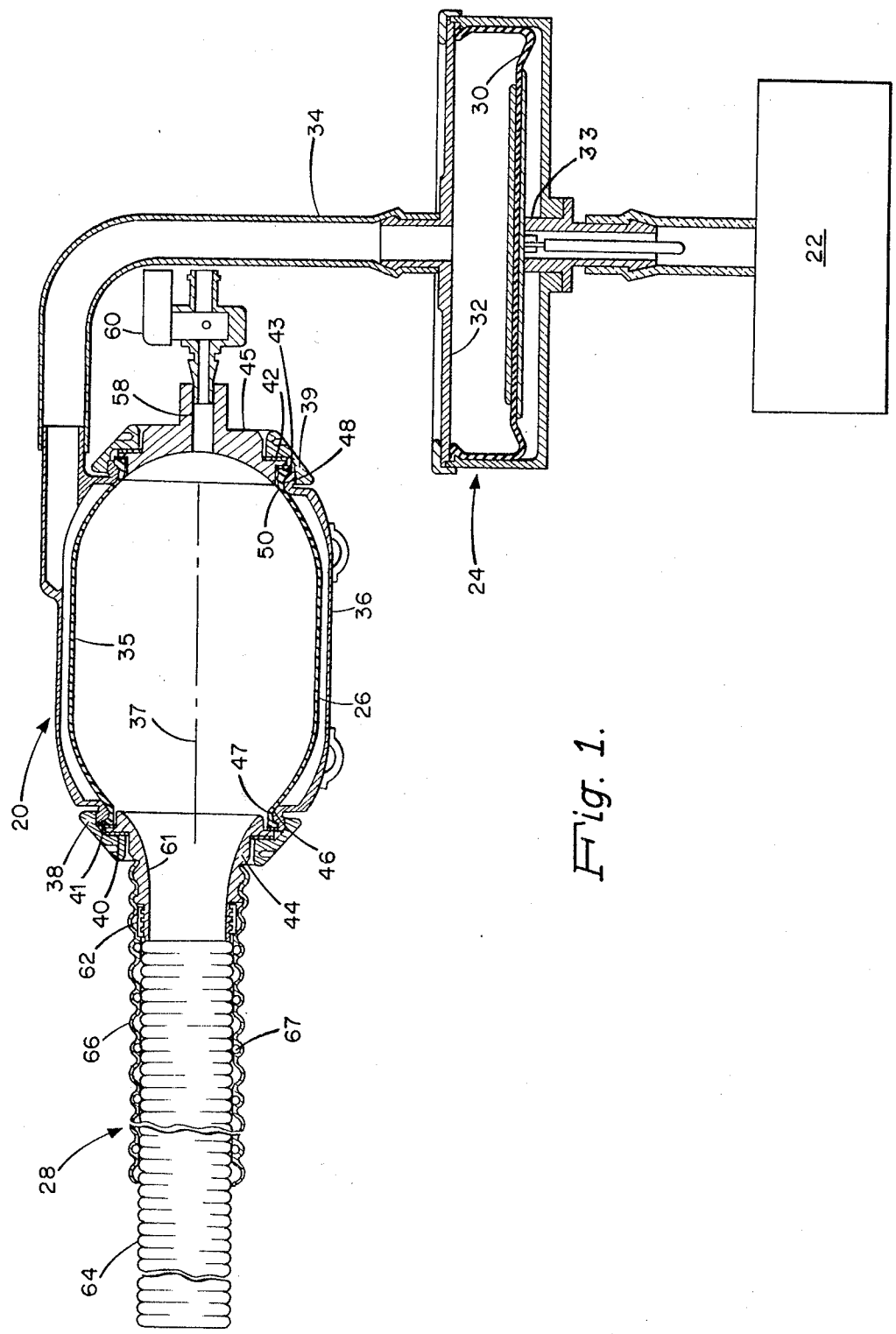
FIG. 1 is a view, partly in section, showing a preferred embodiment of the circulatory assist device of the invention.

A preferred embodiment of the circulatory assist device of the invention is illustrated in FIG. 1 and includes a valveless blood pump 20 which is powered by a pneumatic driver 22. Driver 22 is operable to deliver pressure pulses through a stroke volume limiter 24 to rhythmically compress and release a flexible bladder 26 in pump 20. A flexible conduit 28 is provided for circulating blood between a patient and the interior of bladder 26. Conduit 28 has one end attached to pump 20 and its opposite end is attachable to a major blood vessel of the circulatory system of a patient.

Several of the above-mentioned elements of the circulatory assist device will now be described in detail.

Pneumatic driver 22 may be any source of pressure pulses suitable for rhythmically compressing and releasing bladder 26 at a controlled rate. Preferably driver 22 is capable of operation both in a mode synchronous with the heartbeat rate of a patient by suitable attachment to a electrocardiograph (not shown) and also in a mode producing pulses at a fixed asynchronous rate. Asynchronous operation may be required if, for example, synchronous operation is not possible due to cardiac arrhythmias. One suitable driver is part of Clinical LVAD Drive Console, available from Thermo Electron Corporation, Waltham, Mass.

Figure 3:
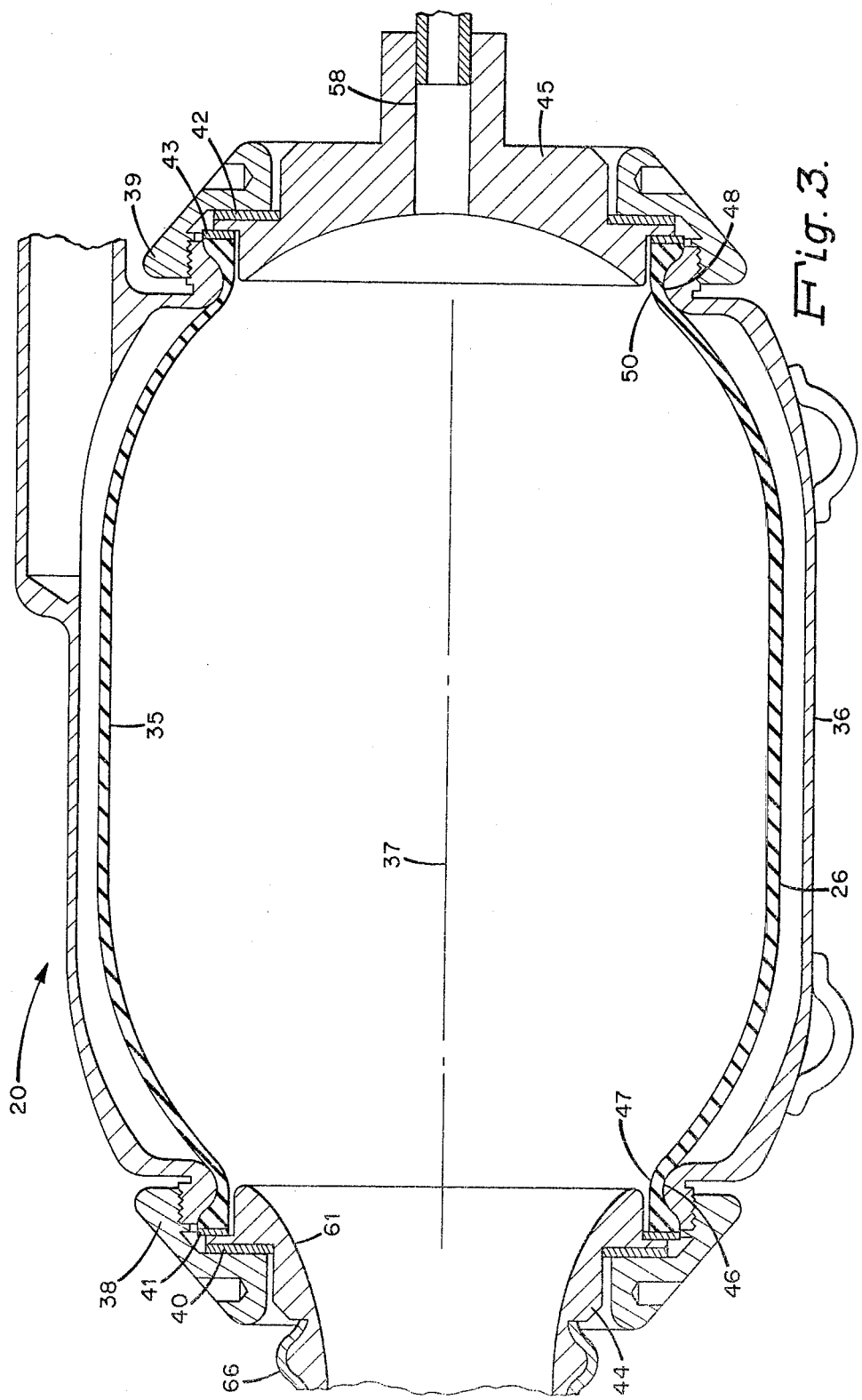
FIG. 3 is a view in cross-section of the pump illustrated in FIG. 1 enlarged to show details such as the sealing arrangements at the ends of the pump.

For safe operation and particularly to limit the maximum movement of the walls of bladder 26 so that the interior surfaces thereof do not touch and damage the blood during pumping, the circulatory assist device includes means for limiting the magnitude of pressure pulses applied to bladder 26 by pneumatic driver 22. This pulse limiting means may be an integral part of pneumatic driver 22 or, as shown in FIG. 1, may be a separate pulse limiter 24 interposed between driver 22 and pump 20 which is shown in FIG. 1 and an enlarged view of which is given in FIG. 3. Pulse limiter 24, a suitable example of which is given in U.S. Pat. No. 4,023,468 issued to V. L. Poirier, whose disclosure is incorporated herein by reference, includes a flexible diaphragm 30 which isolates driver 22 from pump 20 and is allowed to move only within limits established by a fixed wall 32 and a suitable stop means 33. Diaphragm 30 forms part of a closed pneumatic system confining a fixed quantity of compressible gas in the volume between diaphragm 30 and the bladder 26, this volume including the space between the diaphragm 30 and the wall 32, the volume within a flexible tube 34 connecting pulse limiter 24 and pump 20, and the volume between bladder 26 and the rigid housing 36 of pump 20. This confined gas, in conjunction with the limited movement of diaphragm 30, limits the magnitude of the pulses transmitted to bladder 26 to a predetermined maximum independently of the magnitude of the pulses applied by driver 22. The gas in this closed system is preferably carbon dioxide which is inert and readily absorbable by the blood in the event of a leak or rupture in bladder 26.

Pump 20 comprises a flexible bladder 26 generally symmetrical about a longitudinal axis 37 and enclosed in a rigid housing 36. Bladder 26 may be fabricated of polyurethane and have either a smooth or textured inner surface 35. One suitable textured surface is a fibrillar surface fabricated either from polyurethane or adhesively bonded fibrils coated with polyurethane. The textured surface provides a matrix on which blood elements may deposit during use to provide an autogenic, blood-compatible lining to minimize damage to blood circulated into and out of pump 20.

In its relaxed or fully extended position as shown in FIG. 1, bladder 26 is generally spaced a small distance from housing 36 except at the end portions thereof where housing 36 and bladder 26 are sealably held in contact with each other by means of coupling rings 38 and 39. Rings 38 and 39, together with washers 40, 41, 42, 43, an inlet adapter 44 to which the conduit 28 is attached, and an an end cap 45, prevent leakage of blood or compressed gas around the end portions of bladder 26 and housing 36.

Housing 36 and bladder 26 have openings 46 and 47 respectively at the end of pump 20 from which conduit 28 extends, housing opening 46 being substantially coincident with bladder opening 47 but larger in diameter by the wall thickness of the bladder. Bladder opening 47 permits the passage of blood into bladder 26 from conduit 28 through an inlet adaptor 44 as blood is ejected by the heart of the patient being assisted and permits the flow of blood out of bladder 26 as the bladder is compressed by a pressure pulse from driver 22. Similar openings 48 and 50 are provided in the opposite ends of housing 36 and bladder 26 but are sealed against the flow of blood or compressed gas therethrough by means of an end cap 45 and washers 42 and 43. The end cap 45 and washers 42 and 43 are held against bladder 26 by a coupling ring 39 threadedly engaging housing 36. A port 58 is provided in end cap 45 and permits fluid communication between the interior of bladder 26 and a multi-port coupling 60 attached to and extending outwardly from end cap 45 to the exterior of pump 20. Multi-port coupling 60 permits the taking of blood samples or pressure readings and the addition of blood, as for priming of pump 20.

Within the opening 47 of bladder 26, through which blood is admitted and discharged during operation of pump 20, there is positioned one end of inlet adaptor 44 which connects flexible conduit 28 to pump 20 and provides a smooth flowpath for the passage of blood to and from the pump. The inner surface 61 of adaptor 44 tapers in a smooth contour from a diameter substantially equal to that of bladder opening 47 at the end of adaptor 44 connected to pump 20 to a diameter substantially equal to the inner diameter of flexible conduit 28 to which it is attached by threaded connection 62. Surface 61 and the inner surface of end cap 45, like bladder inner surface 35, may be smooth or textured.

Flexible conduit 28 accommodates the flow of blood between pump 20, which is positioned outside of the body of a patient, and a major blood vessel of the patient's circulatory system to which the end of conduit 28 remote from pump 20 is attached. Conduit 28, a suitable example of which is described in U.S. Pat. No. 4,086,665 issued in the name of Victor L. Poirier, preferably comprises an inner graft member 64 extending along its entire length and a protective sleeve 66 which coaxially envelops graft member 64 along at least the portion of conduit 28 which remains external to the patient during use of the circulatory assist device. Graft member 64 is preferably a woven polyester vascular graft and is porous to promote the growth of a stable biological interface to minimize damage to blood during the period of up to a week or two that the device may be required to operate. Protective sleeve 66 is comprised of a flexible impervious material such as silicone rubber and is convoluted for strength. The combination of graft member 64 and protective sleeve 66 allows surgical manipulation of conduit 28 yet minimizes the possibility of contamination of any blood-contacting surface. Reinforcing rings 67 between sleeve 66 and graft member 64 provide additional strength and prevent kinking or distortion of the enclosed graft member 64.

Figure 2:
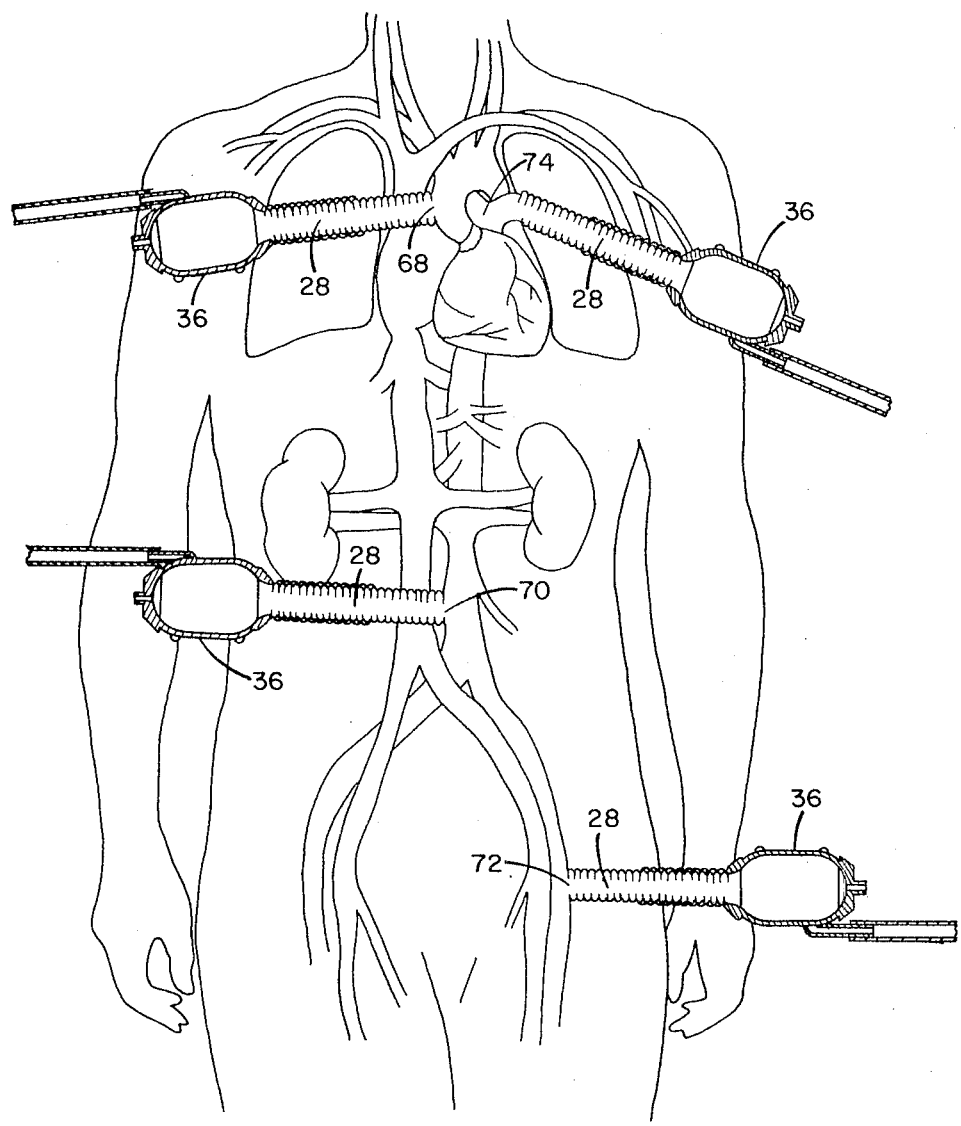
FIG. 2 is a diagrammatic view of a portion of the circulatory system of a patient showing various preferred locations for attachment of the assist device to the circulatory system.

The end of conduit 28 remote from pump 20 is attachable to a major blood vessel of the circulatory system of a patient in the manner and at the locations shown in FIG. 2. This end is sutured to the side of the vessel in an end-to-side attachment so the conduit 28 does not extend into the lumen or cavity of the blood vessel and thus does not interfere with normal blood flow through the vessel. This manner of attachment and the arrangement of the circulatory assist device such that no components except conduit 28 need to be implanted within a patient provide several advantages. First, they permit some choice or flexibility in the location of attachment to the patient and also allow the device to be connected to major vessels of either the right or left heart circulation (or both if there is biventricular dysfunction and the use of two circulatory assist devices appears warranted). Thus, in the event that the left side of the heart fails or otherwise requires support, the circulatory assist device may be connected as shown in FIG. 2 to a left heart position such as the thoracic aorta (68), abdominal aorta (70), or femoral artery (72). If support of the right side of the heart is required, the device may be connected to a right heart position, preferably the main pulmonary artery (74), whose short length precludes use therewith of prior art implantable assist devices. In addition, the device of the present invention may be used not only to assist adults but also to aid children, particularly children weighing 30 pounds or more (and smaller children if the size of pump 20 and conduit 28 are properly selected). A further advantage of the device is the relative ease of implantation, which does not require catherization, multiple connections or placement of a considerable amount of hardware within the body cavity, but merely requires a suturing operation. Removal is also convenient and may be accomplished without major surgery, with only a non-functional stub of graft member 64 remaining in place.

Use and operation of the circulatory assist device will now be reviewed. Conduit 28 is first connected to the blood vessel selected according to the location and type of circulatory problem of the patient—e.g. to the aorta for a left ventricular failure. Pump 20 is then primed by the addition of blood or other fluid such as a saline solution through port 58 in end cap 45 thereof and an electrocardiograph is electrically connected to the patient's heart and to the pneumatic driver 22. If the heartbeat of the patient is irregular, pneumatic driver 22 may be set to produce pressure pulses at a suitable fixed rate to assist in circulating blood. If the heartbeat is regular, driver 22 is set to produce pulses synchronously with the heart—i.e. in response to signals from the electrocardiogram. Thus during synchronous operation as blood is ejected by the heart, conduit 28 and bladder 26 provide a low impedance path and blood flows into bladder 26. After the heart ejects blood and its aortic valve closes a pneumatic pulse is produced by pneumatic driver 22 and transmitted through pulse limiter 24 and flexible tube 34 to the space between housing 36 and bladder 26. The pulse compresses bladder 26, ejecting blood through conduit 28 and providing an extra force to circulate the blood through the system of the patient. The assist device thus assumes as much as fifty percent of the work of the right or left chamber of the heart and by providing this support for a limited period of up to a week or two gives the heart an opportunity to regain sufficient strength to assume the full load of pumping blood. After the circulatory assist device has been used for the desired period, conduit 28 is clamped and tied off near its end-to-side connection to the aorta or other major blood vessel and the remainder of conduit 28 is removed from the patient.

While there have been shown and described what are considered preferred embodiments of the invention, it should be understood that various other modifications may be made therein without departing from the scope of the invention, and thus these preferred embodiments shall be interpreted as illustrative and not in a limiting sense.

What is claimed is:

1. Apparatus for assisting circulation of the blood of a patient comprising:
    a valveless blood pump with a housing positionable outside the patient, said pump including a flexible bladder symmetrical about a longitudinal axis of the pump, said bladder and said housing each having a first opening for admitting blood into and discharging blood from said bladder and each having a second opening for taking samples at an end opposite said first opening, said pump further including means for sealing said second openings;
    a valveless flexible conduit for carrying blood between the interior of said bladder and the circulatory system of the patient, said conduit having a first end attached to said pump adjacent to the first opening of said bladder and an implantable second end attachable to the side of a major blood vessel within the patient on either the right or left side of the patient's heart in a manner such that said conduit terminates without extending into the lumen of said vessel;
    conduit attachment means for connecting said first end of said conduit to said pump; and
    means for compressing and releasing said bladder at a controlled rate.

2. Apparatus as in claim 1 wherein said conduit comprises a polyester vascular graft and a reinforced, convoluted impervious flexible sleeve surrounding said graft along at least that portion of the conduit to be positioned outside of the patient after attachment of said conduit to a blood vessel.

3. Apparatus as in claim 1 wherein said means for sealing the second opening of the bladder comprises an end cap having a passage therethrough and a multi-port coupling attached to said end cap, said coupling adapted for removal of blood samples from said bladder and addition of fluids to said bladder.

4. A blood circulatory assist device comprising:
    a non-implantable, valveless blood pump, said pump including a flexible polyurethane bladder symmetrical about a longitudinal axis of the pump, said bladder and said housing each having (an) a first opening at one end of the pump for admitting and discharging blood and each having a second opening for taking samples at an end opposite said first opening, said pump further including means for sealing said second openings; said rigid housing enclosing and spaced from said bladder, said housing having an opening for admitting pressurized carbon dioxide gas to the space between said housing and said bladder and for discharging the gas from said space;

a valveless flexible conduit for carrying blood between said pump and the circulatory system of a patient, said conduit having a first end attached to said pump adjacent to the first opening of said bladder and a second end attachable to a selected major blood vessel on the right or left side of the patient's heart;

means connecting said first end of said conduit to said pump at a location adjacent said bladder opening and providing a tapered passage for the smooth flow of blood between said conduit and the interior of said bladder;

a pneumatic driver for providing pressure pulses to the opening of said housing to rhythmically compress and release said bladder; and a pulse limiter interposed between said pneumatic driver and the opening of said housing for limiting the maximum magnitude of pressure pulses applied to said bladder independently of the magnitude of pulses generated by said driver.

5. A blood circulatory assist device as in claim 4 wherein said pneumatic driver is operable to provide pressure pulses at a rate synchronous with the heartbeat of the patient.

6. A blood circulatory assist device as in claim 4 wherein said pneumatic driver is operable to provide pressure pulses at a fixed rate asynchronous with the heartbeat of the patient.

* * * * *